(12) United States Patent
Honma

(10) Patent No.: US 8,742,155 B2
(45) Date of Patent: Jun. 3, 2014

(54) PREPARATION OF ORGANOXYSILYL OR SILOXY-CONTAINING ETHYLNORBORNENE COMPOUND

(75) Inventor: Takayuki Honma, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 107 days.

(21) Appl. No.: 13/592,533

(22) Filed: Aug. 23, 2012

(65) Prior Publication Data

US 2013/0066095 A1 Mar. 14, 2013

(30) Foreign Application Priority Data

Sep. 12, 2011 (JP) ................................ 2011-198595

(51) Int. Cl.
*C07F 7/18* (2006.01)
*C07F 7/14* (2006.01)

(52) U.S. Cl.
CPC .... *C07F 7/14* (2013.01); *C07F 7/18* (2013.01)
USPC .......................................... 556/479; 556/462

(58) Field of Classification Search
CPC ............ C07F 7/14; C07F 7/18; C07F 7/0879; C08G 77/08
USPC .................................................. 556/462, 479
See application file for complete search history.

(56) References Cited

U.S. PATENT DOCUMENTS

| 5,191,103 A | * | 3/1993 | Mehta et al. ................... 556/479 |
| 6,943,264 B2 | * | 9/2005 | Kubota et al. ................. 556/440 |
| 2003/0100784 A1 | * | 5/2003 | Giessler et al. ............... 556/473 |

FOREIGN PATENT DOCUMENTS

| JP | 2005-097265 A | 4/2005 |
| JP | 2009-255380 A | 11/2009 |
| WO | 2008/082128 A1 | 7/2008 |

* cited by examiner

*Primary Examiner* — Sudhakar Katakam
*Assistant Examiner* — Pancham Bakshi
(74) *Attorney, Agent, or Firm* — Westerman, Hattori, Daniels & Adrian, LLP

(57) ABSTRACT

When an organoxysilyl or siloxy-containing ethylnorbornene compound is prepared by hydrosilylation of 5-vinyl-2-norbornene with a hydrogen organoxysilane or siloxy compound in the presence of a platinum catalyst, hydrosilylation is conducted in the co-presence of an ammonium salt. The organoxysilyl or siloxy-containing ethylnorbornene compound is effectively prepared at high reactivity and selectivity.

7 Claims, No Drawings

PREPARATION OF ORGANOXYSILYL OR SILOXY-CONTAINING ETHYLNORBORNENE COMPOUND

CROSS-REFERENCE TO RELATED APPLICATION

This non-provisional application claims priority under 35 U.S.C. §119(a) on Patent Application No. 2011-198595 filed in Japan on Sep. 12, 2011, the entire contents of which are hereby incorporated by reference.

TECHNICAL FIELD

This invention relates to a method for preparing organoxysilyl or siloxy-containing ethylnorbornene compounds which are useful as silane coupling agents, surface treating agents, textile treating agents, adhesives, paint additives and the like.

BACKGROUND ART

Organoxysilyl or siloxy-containing ethylnorbornene compounds are very useful for filler addition and siloxane modification which are typical means for improving physical properties of polymers, especially metathesis polymerization polymers (see JP-A 2009-255380 and JP-A 2005-097265).

One known method for preparing organoxysilyl or siloxy-containing ethylnorbornene compounds is hydrosilylation of 5-vinyl-2-norbornene with a hydrogen organoxysilane or siloxy compound (WO 2008/082128). However, the prior art hydrosilylation methods including the method of WO 2008/082128 have poor reactivity and exhibit low selectivity of the target product because a substantial amount of adduct is formed by addition to the endocyclic double bond of norbornene ring. Moreover, since the adduct formed by addition to the endocyclic double bond and the target product have the same molecular weight and hence approximate boiling points, it is difficult to separate them via distillation, leading to reductions of both purity and yield. Formation of a bissilyl adduct by addition to both the double bonds further reduces the yield of the target product.

When hydrosilylation reaction of 5-vinyl-2-norbornene with trimethoxysilane is conducted in the presence of a chloroplatinic acid catalyst, for example, there arises a problem that not only the target product, i.e., 5-(2-trimethoxysilylethyl)-2-norbornene (a) is obtained, but also vinylnorbornyltrimethoxysilane (b) by addition to the endocyclic double bond and bissilyl adduct (c) by addition to both the double bonds form in noticeable amounts.

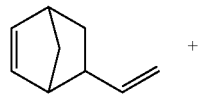

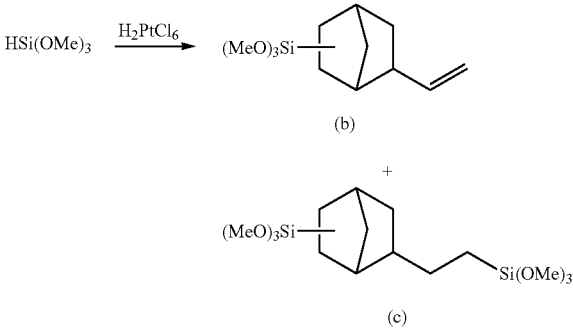

It is necessary to selectively obtain an organoxysilyl or organoxysiloxy-containing ethylnorbornene compound with high purity. If a norbornene compound with low purity is used as a monomer for polymerization, physical properties (specifically, mechanical, thermal, and optical) of the resulting polymer may be reduced or altered. If a vinyl compound is incidentally available during ring-opening metathesis polymerization of norbornene compounds, the vinyl compound may act to stop the ring-opening metathesis polymerization and interfere with molecular weight control. Accordingly, it is desirable to have a method for effectively preparing an organoxysilyl or siloxy-containing ethylnorbornene compound at high purity and selectivity.

CITATION LIST

Patent Document 1: JP-A 2009-255380
Patent Document 2: JP-A 2005-097265 (U.S. Pat. No. 6,943,264)
Patent Document 3: WO 2008/082128

DISCLOSURE OF INVENTION

An object of the invention is to provide a method for preparing an organoxysilyl or organoxysiloxy-containing ethylnorbornene compound by hydrosilylation reaction between 5-vinyl-2-norbornene and a hydrogen organoxysilane or hydrogen organoxysiloxy compound in the presence of a platinum catalyst, which method enables effective preparation by virtue of enhanced reactivity and selective addition to vinyl versus endocyclic double bond.

The invention pertains to hydrosilylation reaction between 5-vinyl-2-norbornene and a hydrogen organoxysilane compound in the presence of a platinum compound-containing catalyst. The inventors have found that both reactivity and selectivity of addition to vinyl versus endocyclic double bond are improved by the co-presence of an ammonium salt, whereby an organoxysilyl or siloxy-containing ethylnorbornene compound can be effectively prepared.

In one aspect, the invention provides a method for preparing an organoxysilyl or organoxysiloxy-containing ethylnorbornene compound having the general formula (2), comprising hydrosilylation of 5-vinyl-2-norbornene with a hydrogen organoxysilane compound or hydrogen organoxysiloxy compound having the general formula (1) in the presence of a platinum compound-containing catalyst and an ammonium salt.

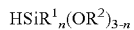  (1)

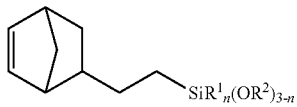  (2)

Herein $R^1$ is a substituted or unsubstituted monovalent hydrocarbon radical of 1 to 10 carbon atoms or siloxy radical, $R^2$ is a substituted or unsubstituted monovalent hydrocarbon radical of 1 to 10 carbon atoms or silyl radical, $R^1$ and $R^2$ each may be the same or different, and n is an integer of 0 to 2.

Preferably, the ammonium salt is an ammonium salt of an acid having pKa of at least 2. Also preferably, the ammonium salt is an ammonium salt of an inorganic acid. Further preferably, the ammonium salt is used in an amount of $1 \times 10^{-5}$ to $1 \times 10^{-1}$ mole per mole of 5-vinyl-2-norbornene.

Preferably, the platinum compound-containing catalyst is a zero valent platinum complex. Also preferably, the platinum compound-containing catalyst is used in an amount to give $1 \times 10^{-7}$ to $1 \times 10^{-2}$ mole of platinum atoms per mole of 5-vinyl-2-norbornene.

Preferably, the hydrogen organoxysilane or siloxy compound having formula (1) is selected from among trimethoxysilane, methyldimethoxysilane, ethyldimethoxysilane, dimethylmethoxysilane, diethylmethoxysilane, triethoxysilane, methyldiethoxysilane, ethyldiethoxysilane, dimethylethoxysilane, diethylethoxysilane, tris(trimethylsiloxy)silane, bis(trimethylsiloxy)methylsilane, 1,1,1,3,3,5,5-hexamethyltrisiloxane, and 1,1,1,3,3,5,5,7,7,9,9-undecamethylpentasiloxane.

Advantageous Effects of Invention

The method involving reacting 5-vinyl-2-norbornene with a hydrogen organoxysilane or siloxy compound in the presence of an ammonium salt has the advantage that the target ethylnorbornene compound having an organoxysilyl or siloxy radical can be effectively prepared at high reactivity and selectivity.

DESCRIPTION OF EMBODIMENTS

One embodiment of the invention is a method for preparing an organoxysilyl or siloxy-containing ethylnorbornene compound having the general formula (2) by effecting hydrosilylation of 5-vinyl-2-norbornene with a hydrogen organoxysilane or siloxy compound having the general formula (1) in the presence of a platinum compound-containing catalyst and an ammonium salt.

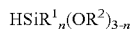  (1)

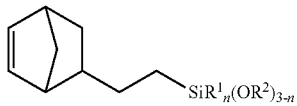  (2)

Herein $R^2$ is a substituted or unsubstituted monovalent hydrocarbon radical of 1 to 10 carbon atoms or siloxy radical, $R^2$ is a substituted or unsubstituted monovalent hydrocarbon radical of 1 to 10 carbon atoms or silyl radical, $R^2$ and $R^2$ each may be the same or different, and n is an integer of 0 to 2.

In formula (1), $R^2$ is a substituted or unsubstituted monovalent hydrocarbon radical of 1 to 10 carbon atoms or a siloxy radical. Examples of the monovalent hydrocarbon radical include straight, branched or cyclic alkyl radicals such as methyl, ethyl, n-propyl, isopropyl, n-butyl, isobutyl, tert-butyl, sec-butyl, n-pentyl, isopentyl, neopentyl, cyclopentyl, n-hexyl, isohexyl, cyclohexyl, n-heptyl, isoheptyl, n-octyl, isooctyl, tert-octyl, n-nonyl, isononyl, n-decyl and isodecyl, aryl radicals such as phenyl, tolyl and xylyl, aralkyl radicals such as benzyl, methylbenzyl, phenethyl, methylphenethyl and phenylbenzyl, straight, branched or cyclic alkenyl radicals such as vinyl, allyl, butenyl, pentenyl, hexenyl, heptenyl, octenyl, nonyl, decenyl and cyclohexenyl, and other monovalent unsaturated aliphatic hydrocarbon radicals.

Also included are substituted forms of these monovalent hydrocarbon radicals in which one or more hydrogen atoms are substituted by substituents. Exemplary substituents include halogen atoms such as fluorine, chlorine and bromine, acyl radicals such as acetyl and benzoyl, acyloxy radicals such as acetoxy and benzoyloxy, amido radicals such as acetamido and benzamido, ester radicals such as methoxycarbonyl and ethoxycarbonyl, organoxy radicals such as methoxy, ethoxy, isopropoxy, tert-butoxy, methoxyethoxy, ethoxyethoxy, phenoxy and benzyloxy, substituted amino radicals such as dimethylamino, diethylamino, diethylaminoethylamino, phenylamino and diphenylamino as well as cyano, nitro, ester, ether, (meth)acryloxy, glycidoxy, epoxy, oxetanyl, sulfide, triorganoxysilyl, dialkylorganoxysilyl, alkyldiorganoxysilyl, and alkylsiloxy radicals.

Examples of the siloxy radical include siloxy radicals having the formula: $-O[Si(CH_3)_2O]_m-Si(CH_3)_3$ wherein m is an integer of 0 to 10.

In formula (1), $R^2$ is a substituted or unsubstituted monovalent hydrocarbon radical of 1 to 10 carbon atoms or a silyl radical. Examples of the monovalent hydrocarbon radical are as exemplified for $R^1$. Examples of the silyl radical include trialkylsilyl, alkylalkoxysilyl, and trialkoxysilyl radicals in which each alkyl moiety has 1 to 4 carbon atoms. Of these, trimethylsilyl is preferred.

Examples of the hydrogen organoxysilane or siloxy compound having formula (1) include trimethoxysilane, methyldimethoxysilane, ethyldimethoxysilane, dimethylmethoxysilane, diethylmethoxysilane, triethoxysilane, methyldiethoxysilane, ethyldiethoxysilane, dimethylethoxysilane, diethylethoxysilane, tris(trimethylsiloxy)silane, bis(trimethylsiloxy)methylsilane, 1,1,1,3,3,5,5-hexamethyltrisiloxane, and 1,1,1,3,3,5,5,7,7,9,9-undecamethylpentasiloxane. In the practice of the invention, 5-vinyl-2-norbornene and the hydrogen organoxysilane or siloxy compound having formula (1) may be combined in any desired ratio. It is preferred from the aspect of economy that the hydrogen organoxysilane or siloxy compound be used in an amount of 0.8 to 3.0 moles, more preferably 1.0 to 1.2 moles per mole of 5-vinyl-2-norbornene.

Suitable ammonium salts include ammonium salts of organic and inorganic acids. Examples of the organic acid ammonium salt include ammonium methanesulfonate, ammonium p-toluenesulfonate, ammonium trifluoromethanesulfonate, ammonium formate, ammonium acetate, ammonium trifluoroacetate, diammonium oxalate, ammonium hydrogenoxalate, ammonium benzoate, monoammonium citrate, diammonium citrate, triammonium citrate, ammonium lactate, ammonium phthalate, ammonium succinate, monoammonium tartrate, diammonium tartrate, and ammonium aspartate. Examples of the inorganic acid ammonium salt include ammonium chloride, ammonium sulfate, ammonium amidosulfate, ammonium nitrate, monoammonium dihydrogenphosphate, diammonium hydrogenphosphate, triammonium phosphate, ammonium hypophosphite, ammonium carbonate, ammonium hydrogencarbonate, ammonium sulfide, ammonium borate and ammonium fluoroborate.

Ammonium salts of acids having pKa of at least 2 are preferred. Ammonium salts of inorganic acid are preferred to ammonium salts of organic acid because use of organic acid ammonium salts is accompanied by formation of an extra compound by ester exchange between the silyl radical of the target compound and the organic acid. Specifically, ammonium carbonate and ammonium hydrogencarbonate are most preferred.

Although the amount of the ammonium salt used is not particularly limited, it is preferred from the aspects of reactivity, selectivity and cost that the ammonium salt be used in an amount of $1 \times 10^{-5}$ to $1 \times 10^{-1}$ mole, more preferably $1 \times 10^{-4}$ to $5 \times 10^{-2}$ mole per mole of 5-vinyl-2-norbornene.

Although the platinum compound-containing catalyst used herein is not particularly limited, suitable examples include chloroplatinic acid, an alcohol solution of chloroplatinic acid, a toluene or xylene solution of platinum-1,3-divinyl-1,1,3,3-tetramethyldisiloxane complex, tetrakis(triphenylphosphine)platinum, dichlorobis(triphenylphosphine)platinum, dichlorobis(acetonitrile)platinum, dichlorobis(benzonitrile)platinum, dichloro(cyclooctadiene)platinum, and supported catalysts such as platinum-on-carbon, platinum-on-alumina and platinum-on-silica catalysts. Among others, zero valent platinum complexes are preferred for selectivity, with a toluene or xylene solution of platinum-1,3-divinyl-1,1,3,3-tetramethyldisiloxane complex being more preferred.

The amount of the platinum compound-containing catalyst used is not particularly limited. From the aspects of reactivity and productivity, the platinum compound-containing catalyst is preferably used in an amount to give $1 \times 10^{-7}$ to $1 \times 10^{-2}$ mole, more preferably $1 \times 10^{-7}$ to $1 \times 10^{-3}$ mole, and most preferably $1 \times 10^{-6}$ to $1 \times 10^{-3}$ mole of platinum atoms per mole of 5-vinyl-2-norbornene.

Although the reaction may take place in a solventless system, solvents may be used. Examples of the solvent used include hydrocarbon solvents such as pentane, hexane, cyclohexane, heptane, isooctane, benzene, toluene and xylene, ether solvents such as diethyl ether, tetrahydrofuran and dioxane, ester solvents such as ethyl acetate and butyl acetate, aprotic polar solvents such as N,N-dimethylformamide, and chlorinated hydrocarbon solvents such as dichloromethane and chloroform. These solvents may be used alone or in admixture of two or more.

In addition, other additives may be used. Suitable additives include tertiary amine compounds and nitrile compounds.

Non-limiting examples of the tertiary amine compound include alkylamine compounds such as triethylamine, tributylamine and diisopropylethylamine, amine compounds having a nitrogen-containing aromatic ring such as pyridine, quinoline and 2,6-lutidine, and special cyclic amines such as 1,8-diazabicyclo[5.4.0]-7-undecene, 1,4-diazabicyclo[2.2.2]octane and hexamethylenetetramine. The amount of the tertiary amine compound used is not particularly limited. The tertiary amine compound is preferably used in an amount of 1 to 1,000 moles, more preferably 1 to 100 moles, and most preferably 1 to 10 moles per mole of the platinum compound-containing catalyst because too much amounts of the tertiary amine compound may largely detract from catalytic activity.

Non-limiting examples of the nitrile compound include acetonitrile, propionitrile, butyronitrile, isobutyronitrile, valeronitrile, acrylonitrile, succinonitrile, 3-methoxypropionitrile, ethylene cyanohydrin, and benzonitrile. The nitrile compound is preferably used in an amount equal to or more than 0.1%, more preferably equal to or more than 0.5%, and most preferably equal to or more than 1% by weight based on 5-vinyl-2-norbornene in order to enhance selectivity. The upper limit is not particularly limited, although the preferred amount is equal to or less than 100%, more preferably equal to or less than 50% by weight. Too small amounts of the nitrile compound may achieve least improvement in selectivity whereas too much amounts of the nitrile compound may lead to a lower yield per volume.

The reaction temperature is not particularly limited, that is, the reaction may be performed either at room temperature or at elevated temperature. Elevated temperature is preferred because an appropriate reaction rate is achievable. The reaction temperature is preferably in a range of 0° C. to 200° C., more preferably 40° C. to 110° C., and most preferably 40° C. to 90° C. The reaction time is preferably 1 to 60 hours, more preferably 1 to 30 hours, and most preferably 1 to 20 hours, though not limited thereto.

The organosilicon compound obtained from the method of the invention may be purified prior to use. Any of various purification methods such as distillation, filtration, washing, column separation and solid adsorbent may be selected depending on the desired quality. For example, distillation purification is preferably used to remove minor impurities such as catalysts and increase the purity of the compound.

The organosilicon compound can be used in any desired applications, examples of which include, but are not limited to, surface treatment of inorganic fillers, liquid sealants, casting molds, surface modification of resins, polymer modifiers, and additives to aqueous coating compositions. In such applications, at least one additive selected from pigments, defoamers, lubricants, antiseptics, pH control agents, film formers, antistatic agents, anti-fungus agents, surfactants, dyes and the like may be added to the organosilicon compound as long as the benefits of the invention are not impaired.

EXAMPLE

Examples of the invention are given below by way of illustration and not by way of limitation.

Example 1

A flask equipped with a thermometer, condenser, stirrer and dropping funnel was charged with 120 g (1.0 mole) of 5-vinyl-2-norbornene, an amount ($1 \times 10^{-4}$ mole of platinum atoms per mole of 5-vinyl-2-norbornene) of toluene solution of platinum-1,3-divinyl-1,1,3,3-tetramethyldisiloxane complex, and 0.4 g (0.005 mole) of ammonium hydrogencarbonate. To the flask at an internal temperature of 55-65° C., 124 g (1.0 mole) of trimethoxysilane was added dropwise over 4 hours. The contents were stirred for one hour at the temperature. On analysis by gas chromatography, the percentage conversion of 5-vinyl-2-norbornene was 98%. The ratio in area % of 5-(2-trimethoxysilylethyl)-2-norbornene:5-vinylnorbornyltrimethoxysilane:bissilyl adduct formed by addition to both endocyclic olefin and vinyl was 95.3:0.1:4.6. The reaction solution was distilled, collecting 218 g of 5-(2-trimethoxysilylethyl)-2-norbornene at a boiling point of 102-103° C./0.4 kPa (yield 90%, purity 99.9%).

Comparative Example 1

Reaction was performed as in Example 1 except that ammonium hydrogencarbonate was not used. Exothermic reaction ceased in the middle of the course, and the dropwise addition was interrupted at that point. On analysis by gas chromatography, the percentage conversion of 5-vinyl-2-norbornene was 29%. The ratio in area % of 5-(2-trimethoxysilylethyl)-2-norbornene:vinylnorbornyltrimethoxysilane:bissilyl adduct formed by addition to both endocyclic olefin and vinyl was 46.9:48.1:5.0.

Example 2

Reaction was performed as in Example 1 except that 0.8 g (0.01 mole) of ammonium hydrogencarbonate was used. On analysis by gas chromatography, the percentage conversion of 5-vinyl-2-norbornene was 99%. The ratio in area % of 5-(2-trimethoxysilylethyl)-2-norbornene:vinylnorbornyltrimethoxysilane:bissilyl adduct formed by addition to both endocyclic olefin and vinyl was 95.3:0.1:4.6.

The reaction solution was distilled, collecting 220 g of 5-(2-trimethoxysilylethyl)-2-norbornene at a boiling point of 102-103° C./0.4 kPa (yield 91%, purity 99.9%).

Example 3

Reaction was performed as in Example 1 except that 0.6 g (0.01 mole) of ammonium acetate was used instead of 0.4 g (0.005 mole) of ammonium hydrogencarbonate. On analysis by gas chromatography, the percentage conversion of 5-vinyl-2-norbornene was 98%. The ratio in area % of 5-(2-trimethoxysilylethyl)-2-norbornene:vinylnorbornyltrimethoxysilane:bissilyl adduct formed by addition to both endocyclic olefin and vinyl was 95.2:0.1:4.7. The reaction solution was distilled, collecting 220 g of 5-(2-trimethoxysilylethyl)-2-norbornene at a boiling point of 102-103° C./0.4 kPa (yield 90%, purity 98.8%, inclusive of 1% 5-(2-acetoxydimethoxysilylethyl)-2-norbornene).

Example 4

Reaction was performed as in Example 1 except that 136 g (1.0 mole) of methyldiethoxysilane was used instead of 124 g (1.0 mole) of trimethoxysilane. On analysis by gas chromatography, the percentage conversion of 5-vinyl-2-norbornene was 96%. The ratio in area % of 5-(2-methyldiethoxysilylethyl)-2-norbornene:vinylnorbornylmethyldiethoxysilane:bissilyl adduct formed by addition to both endocyclic olefin and vinyl was 92.5:0.9:6.6. The reaction solution was distilled, collecting 208 g of 5-(2-methyldiethoxysilylethyl)-2-norbornene at a boiling point of 107-108° C./0.4 kPa (yield 82%, purity 99.0%).

Example 5

Reaction was performed as in Example 1 except that 148 g (1.0 mole) of pentamethyldisiloxane was used instead of 124 g (1.0 mole) of trimethoxysilane. On analysis by gas chromatography, the percentage conversion of 5-vinyl-2-norbornene was 94%. The ratio in area % of 5-(2-dimethyltrimethylsiloxysilylethyl)-2-norbornene:vinylnorbornyldimethyltrimethylsiloxysilane:bissilyl adduct formed by addition to both endocyclic olefin and vinyl was 89.0:1.0:10.0. The reaction solution was distilled, collecting 212 g of 5-(2-dimethyltrimethylsiloxysilylethyl)-2-norbornene at a boiling point of 98-99° C./0.4 kPa (yield 79%, purity 99.0%).

Japanese Patent Application No. 2011-198595 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing an organoxysilyl or organoxysiloxy-containing ethylnorbornene compound having the general formula (2), comprising hydrosilylation of 5-vinyl-2-norbornene with a hydrogen organoxysilane compound or hydrogen organoxysiloxy compound having the general formula (1) in the presence of a platinum compound-containing catalyst and an ammonium salt, $$HSiR^1{}_n(OR^2)_{3-n} \qquad (1)$$

wherein $R^1$ is a substituted or unsubstituted monovalent hydrocarbon radical of 1 to 10 carbon atoms or siloxy radical, $R^2$ is a substituted or unsubstituted monovalent hydrocarbon radical of 1 to 10 carbon atoms or silyl radical, $R^1$ and $R^2$ each may be the same or different, and n is an integer of 0 to 2,

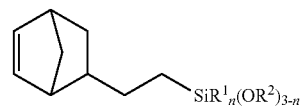

(2)

wherein $R^1$, $R^2$, and n are as defined above.

2. The method of claim 1 wherein the ammonium salt is an ammonium salt of an acid having pKa of at least 2.

3. The method of claim 1 wherein the ammonium salt is an ammonium salt of an inorganic acid.

4. The method of claim 1 wherein the ammonium salt is used in an amount of $1\times10^{-5}$ to $1\times10^{-1}$ mole per mole of 5-vinyl-2-norbornene.

5. The method of claim 1 wherein the platinum compound-containing catalyst is a zero valent platinum complex.

6. The method of claim 1 wherein the platinum compound-containing catalyst is used in an amount to give $1\times10^{-7}$ to $1\times10^{-2}$ mole of platinum atoms per mole of 5-vinyl-2-norbornene.

7. The method of any one of claims 1 to 6 wherein the hydrogen organoxysilane or siloxy compound having formula (1) is selected from the group consisting of trimethoxysilane, methyldimethoxysilane, ethyldimethoxysilane, dimethylmethoxysilane, diethylmethoxysilane, triethoxysilane, methyldiethoxysilane, ethyldiethoxysilane, dimethylethoxysilane, diethylethoxysilane, tris(trimethylsiloxy)silane, bis(trimethylsiloxy)methylsilane, 1,1,1,3,3,5,5-hexamethyltrisiloxane, and 1,1,1,3,3,5,5,7,7,9,9-undecamethylpentasiloxane.

* * * * *